United States Patent
Yoo

(10) Patent No.: US 12,236,591 B2
(45) Date of Patent: Feb. 25, 2025

(54) METHOD AND SYSTEM FOR PARALLEL PROCESSING FOR MEDICAL IMAGE

(71) Applicant: LUNIT INC., Seoul (KR)

(72) Inventor: Donggeun Yoo, Seoul (KR)

(73) Assignee: LUNIT INC., Seoul (KR)

( * ) Notice: Subject to any disclaimer, the term of this patent is extended or adjusted under 35 U.S.C. 154(b) by 378 days.

(21) Appl. No.: 17/885,611

(22) Filed: Aug. 11, 2022

(65) Prior Publication Data

US 2023/0052847 A1 Feb. 16, 2023

(30) Foreign Application Priority Data

Aug. 11, 2021 (KR) .................. 10-2021-0105889
Feb. 21, 2022 (KR) .................. 10-2022-0022243

(51) Int. Cl.
| | |
|---|---|
| G16H 70/60 | (2018.01) |
| G06T 7/00 | (2017.01) |
| G06V 10/22 | (2022.01) |
| G06V 10/774 | (2022.01) |
| G16H 30/40 | (2018.01) |

(52) U.S. Cl.
CPC ............ *G06T 7/0012* (2013.01); *G06V 10/22* (2022.01); *G06V 10/774* (2022.01); *G16H 30/40* (2018.01); *G16H 70/60* (2018.01); *G06T 2207/20081* (2013.01); *G06T 2207/30004* (2013.01); *G06V 2201/03* (2022.01)

(58) Field of Classification Search
CPC ......... G06T 7/0012; G06T 2207/20081; G06T 2207/30004; G06V 10/22; G06V 10/774; G06V 2201/03; G06V 10/82; G16H 30/40; G16H 70/60; G16H 50/70; G16H 50/20; G06F 9/3877; G06N 3/08; G06N 3/084

See application file for complete search history.

(56) References Cited

U.S. PATENT DOCUMENTS

| | | | |
|---|---|---|---|
| 11,853,391 B1* | 12/2023 | Ladkat | G06N 3/063 |
| 2020/0003886 A1* | 1/2020 | Cho | G06N 20/00 |
| 2020/0163641 A1* | 5/2020 | Amit | A61B 6/502 |
| 2020/0233493 A1* | 7/2020 | Bott | G06V 40/161 |
| 2021/0006755 A1* | 1/2021 | Kim | H04N 23/667 |
| 2021/0118136 A1* | 4/2021 | Hassan-Shafique | G16B 20/20 |
| 2021/0374518 A1* | 12/2021 | Zhu | G06T 7/10 |
| 2021/0398326 A1* | 12/2021 | Lee | G06N 3/045 |
| 2022/0309708 A1* | 9/2022 | Bhate | G06T 7/20 |

(Continued)

*Primary Examiner* — Cindy Trandai
(74) *Attorney, Agent, or Firm* — Sughrue Mion, PLLC

(57) ABSTRACT

A method for parallel processing a digitally scanned pathology image is performed by a plurality of processors and includes performing, by a first processor, a first operation of generating a first batch from a first set of patches extracted from a digitally scanned pathology image and providing the generated first batch to a second processor, performing, by the first processor, a second operation of generating a second batch from a second set of patches extracted from the digitally scanned pathology image and providing the generated second batch to the second processor, and performing, by the second processor, a third operation of outputting a first analysis result from the first batch by using a machine learning model, with at least part of time frame for the second operation performed by the first processor overlapping at least part of time frame for the third operation performed by the second processor.

20 Claims, 12 Drawing Sheets

(56) References Cited

U.S. PATENT DOCUMENTS

2022/0319006 A1* 10/2022 Annangi ............ G06F 18/2148
2023/0162316 A1* 5/2023 Kim ........................ G06N 3/08
                                                                    382/307

\* cited by examiner

METHOD AND SYSTEM FOR PARALLEL PROCESSING FOR MEDICAL IMAGE

CROSS-REFERENCE TO RELATED APPLICATION

This application claims priority to Korean Patent Application No. 10-2021-0105889, filed in the Korean Intellectual Property Office on Aug. 11, 2021, and Korean Patent Application No. 10-2022-0022243, filed in the Korean Intellectual Property Office on Feb. 21, 2022, the entire contents of which are hereby incorporated by reference.

TECHNICAL FIELD

The present disclosure relates to a method and a system for parallel processing a medical image by using a plurality of processors, and more particularly, to a method and a system for outputting an analysis result from at least one patch in the medical image by using a plurality of processors.

BACKGROUND

Recently, the development of a medical artificial intelligence solution is receiving increasing attention, which analyzes a wide range of medical data including medical image data and pathology images such as X-ray image data, computer tomography (CT) image data, and magnetic resonance imaging (MRI) data, and helps medical practitioners diagnose. Such medical artificial intelligence solution is expected to contribute to resolving the current trend in which medical staff supply becomes short while medical demand increases due to rapid aging of the population.

Meanwhile, accurate medical image reading and medical diagnosis are important to increase the utilization of the medical artificial intelligence solution, but it is also important to provide patients in the medical environment with the information quickly and rapidly. However, because medical data is generally a high-resolution image that has a very large data size, and because it requires the processing of complicated computations in the computing system, it may take a considerable amount of time until the results are derived. Accordingly, designing a fast and efficient medical image processing method can provide further advancement of the medical artificial intelligence solution.

SUMMARY

In order to address one or more problems (e.g., the problems described above and/or other problems not explicitly described herein), the present disclosure provides a method for parallel processing a medical image by using a plurality of processors.

The present disclosure may be implemented in a variety of ways, including a method, an apparatus (or system), or a non-transitory computer-readable recording medium storing instructions.

There is provided a method for parallel processing a digitally scanned pathology image, which may be performed by a plurality of processors and include performing, by a first processor, a first operation of generating a first batch from a first set of patches extracted from a digitally scanned pathology image and providing the generated first batch to a second processor, performing, by the first processor, a second operation of generating a second batch from a second set of patches extracted from the digitally scanned pathology image and providing the generated second batch to a second processor, and performing, by the second processor, a third operation of outputting a first analysis result from the first batch by using a machine learning model. In an example, at least a part of a time frame for the second operation performed by the first processor may overlap with at least a part of a time frame for the third operation performed by the second processor.

The method may further include performing, by the second processor, a fourth operation of outputting a second analysis result from the second batch by using the machine learning model, in which medical information associated with the digitally scanned pathology image may be generated based on the first analysis result and the second analysis result.

The digitally scanned pathology image may include a plurality of digitally scanned reference pathology images, and the machine learning model may be trained by using a plurality of batches and a plurality of reference analysis results in the plurality of digitally scanned reference pathology images.

The digitally scanned pathology image may include segmentation information for a specific object in the digitally scanned pathology image. The performing the first operation may include extracting a first set of patches that include the specific object, and generating a first batch including the extracted first set of patches.

The first set of patches and the second set of patches may be spatially associated with each other in the digitally scanned pathology image.

Each of at least one patch included in the first set of patches and each of at least one patch included in the second set of patches may be adjacent to each other or overlapped with each other at least in part in the digitally scanned pathology image.

Each of the first set of patches associated with the first batch and the second set of patches associated with the second batch may include spatial information in the digitally scanned pathology image, a processed image may be generated based on the spatial information associated with each of the first set of patches and the second set of patches, and the medical information associated with the digitally scanned pathology image may be generated based on the first analysis result, the second analysis result, and the processed pathology image.

The generated medical information may include statistical information of the digitally scanned pathology image.

The performing the first operation may include performing, by the first processor, image processing on the generated first batch, the performing the second operation may include performing, by the first processor, image processing on the generated second batch, and the image processing on the first batch and the image processing on the second batch may include at least one of contrast adjustment, brightness adjustment, saturation adjustment, blur adjustment, noise injection, random crop, or sharpening.

According to another example, a method for parallel processing a digitally scanned pathology image is provided, which may be performed by a plurality of processors and include performing, by a first processor, a first operation of generating a first batch from one or more first patches of a plurality of patches stored in a storage medium and providing the generated first batch to a second processor, performing, by the first processor, a second operation of generating a second batch from one or more second patches of the plurality of patches stored in the storage medium and providing the generated second batch to the second processor, and performing, by the second processor, a third operation of outputting a first analysis result from the first batch by using a machine learning model. In an example, at least a part of a time frame for the second operation performed by the first processor may overlap with at least a part of a time frame for the third operation performed by the second processor.

There may be provided a non-transitory computer-readable recording medium storing instructions for executing, on a computer, the method described above.

An information processing system may be provided, which may include a memory, and a first processor and a second processor connected to the memory and configured to execute at least one computer-readable program included in the memory, in which the at least one program may include instructions for performing, by the first processor, a first operation of generating a first batch from a first set of patches extracted from a digitally scanned pathology image and providing the generated first batch to the second processor, performing, by the first processor, a second operation of generating a second batch from a second set of patches extracted from the digitally scanned pathology image and providing the generated second batch to the second processor, performing, by the second processor, a third operation of outputting a first analysis result from the first batch by using the machine learning model. In an example, at least a part of a time frame for the second operation performed by the first processor may overlap with at least a part of a time frame for the third operation performed by the second processor.

An information processing system according to another example is provided, which may include a memory, and a first processor and a second processor connected to the memory and configured to execute at least one computer-readable program included in the memory, in which the at least one program may include instructions for performing, by the first processor, a first operation of generating a first batch from one or more first patches of a plurality of patches stored in a storage medium and providing the generated first batch to second processor, performing, by the first processor, a second operation of generating a second batch from one or more second patches of the plurality of patches stored in the storage medium and providing the generated second batch to the second processor, and performing, by the second processor, a third operation of outputting a first analysis result from the first batch by using a machine learning model. In an example, at least a part of a time frame for the second operation performed by the first processor may overlap with at least a part of a time frame for the third operation performed by the second processor.

According to some examples, by parallel processing a medical image, the amount of operations and computations that one processor has to handle can be reduced.

According to some examples, by parallel processing a medical image, the time required for generating medical information from the medical image by using the machine learning model or training the machine learning model can be reduced.

According to some examples, by selectively extracting only the patches associated with a specific object from the medical image and using the same as training data, the performance of a machine learning model for inferring an analysis result associated with the specific object can be significantly improved.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION

Figure 1:
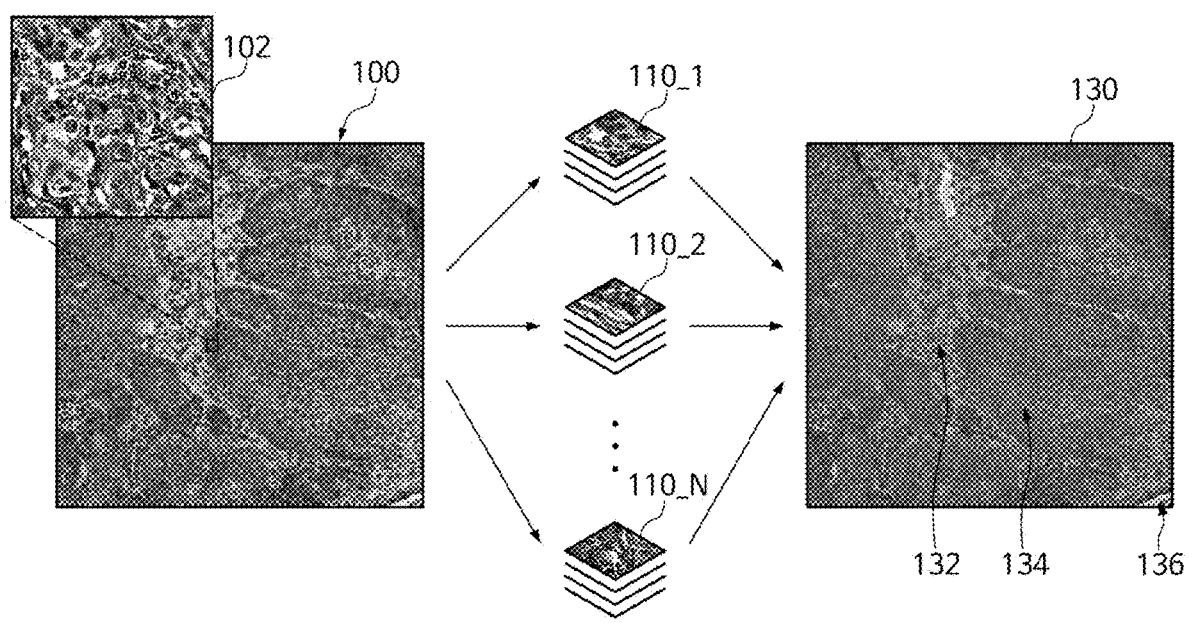
FIG. 1 illustrates an example of generating medical information associated with a medical image from the medical image.

Hereinafter, example details for the practice of the present disclosure will be described in detail with reference to the accompanying drawings. However, in the following description, detailed descriptions of well-known functions or configurations will be omitted when it may make the subject matter of the present disclosure rather unclear.

In the accompanying drawings, the same or corresponding components are assigned the same reference numerals. In addition, in the following description of the various examples, duplicate descriptions of the same or corresponding components may be omitted. However, even if descriptions of components are omitted, it is not intended that such components are not included in any embodiment.

Advantages and features of the disclosed examples and methods of accomplishing the same will be apparent by referring to examples described below in connection with the accompanying drawings. However, the present disclosure is not limited to the examples disclosed below, and may be implemented in various forms, and the examples are merely provided to make the present disclosure complete, and to fully disclose the scope of the invention to those skilled in the art to which the present disclosure pertains.

The terms used herein will be briefly described prior to describing the disclosed embodiment(s) in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the embodiment(s). Therefore, the terms used in the present disclosure should be defined based on the meaning of the terms and the overall content of the present disclosure rather than a simple name of each of the terms.

As used herein, the singular forms "a," "an," and "the" are intended to include the plural forms as well, unless the context clearly indicates the singular forms. Further, the plural forms are intended to include the singular forms as well, unless the context clearly indicates the plural forms. Further, throughout the description, when a portion is stated as "comprising (including)" a component, it intends to mean that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to play one or more processors. Accordingly, as an example, the "module" or "unit" may include components such as software components, object-oriented software components, class components, and task components, and at least one of processes, functions, attributes, procedures, subroutines, segments of program code, drivers, firmware, micro-codes, circuits, data, database, data structures, tables, arrays, or variables. Furthermore, functions provided in the components and the "modules" or "units" may be combined into a smaller number of components and "modules" or "units", or further divided into additional components and "modules" or "units."

The "module" or "unit" may be implemented as a processor and a memory. The "processor" should be interpreted broadly to encompass a general-purpose processor, a central processing unit (CPU), a microprocessor, a digital signal processor (DSP), a controller, a microcontroller, a state machine, and so forth. Under some circumstances, the "processor" may refer to an application-specific integrated circuit (ASIC), a programmable logic device (PLD), a field-programmable gate array (FPGA), and so on. The "processor" may refer to a combination for processing devices, e.g., a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and so on. The memory is said to be in electronic communication with a processor if the processor can read information from and/or write information to the memory. The memory integrated with the processor is in electronic communication with the processor.

In the present disclosure, an "accelerator" may refer to any processor for performing an operation required in a machine learning model, and for example, the "accelerator" may refer to a graphic processing unit (hereinafter referred to as "GPU"), a field programmable gate array (hereinafter referred to as "FPGA"), and the like, but is not limited thereto.

In the present disclosure, a "system" may refer to at least one of a server device and a cloud device, but not limited thereto. For example, the system may include one or more server devices. In another example, the system may include one or more cloud devices. In still another example, the system may include both the server device and the cloud device operated in conjunction with each other.

In the present disclosure, a "medical image" may refer to any image associated with a human body, human tissue and/or human specimen. For example, the medical image may be a 2D image or a 3D image. The medical image may include a 2D frame and/or a 3D frame.

The medical image may include a "pathology image" obtained by capturing an image of a tissue removed from the human body. In an example, the pathology image may refer to an image obtained by capturing an image of a pathology slide that is fixed and stained through a series of chemical treatments with respect to the tissue removed from the human body. In addition, the pathology image may refer to a whole slide image (WSI) including a high-resolution image with respect to an entire slide, and at least one of hematoxylin & eosin (H&E) stained slide or immunohistochemistry (IHC) stained slide. The pathology image may refer to a part of the entire high resolution slide image, such as one or more patches, for example. For example, the pathology image may refer to a digital image captured or scanned through a scanning device (e.g., a digital scanner, and the like), and may include information of specific proteins, cells, tissues, and/or structures in the human body. Further, the pathology image may include one or more patches, and the one or more patches may be applied (e.g., tagged) with the histological information through annotation work.

In another embodiment, the medical image may refer to an X-ray image, a computed tomography (CT) image, or a magnetic resonance imaging (MRI) image obtained by scanning or capturing an image of a human body.

In the present disclosure, the "patch" may refer to a small region in the pathology slide image. In an example, the patch may include a training patch used in the process of training the machine learning model and/or a patch used in the inference process of the machine learning model. For example, the patch may include a region corresponding to a semantic object extracted by performing segmentation on a medical image. As another example, the patch may refer to a combination of pixels associated with the histological information generated by analyzing the medical image.

In the present disclosure, a "batch" may include a set of patches. In an example, "a set" may refer to one or more patches.

In the present disclosure, the "machine learning model" may include any model that is used to infer an answer to a given input. In the present disclosure, various machine learning methods such as supervised learning, unsupervised learning, reinforcement learning, and the like may be used. The machine learning model may include an artificial neural network model including an input layer, a plurality of hidden layers, and an output layer. In an example, each layer may include one or more nodes. For example, the machine learning model may be trained to infer an analysis result (e.g., histological information, and the like) for a medical image and/or at least one patch included in the medical image. In this case, the histological information generated through the annotation work may be used for training the machine learning model. As another example, the machine learning model may be trained to infer an analysis result and/or medical information based on characteristics of at least one of a cell, a tissue, or a structure in the medical image. In addition, the machine learning model may include weights associated with a plurality of nodes included in the machine learning model. In an example, the weights may include any parameter associated with the machine learning model.

In the present disclosure, the machine learning model may refer to an artificial neural network model, and the artificial neural network model may refer to the machine learning model.

In the present disclosure, "training" may refer to any process of changing weights included in the machine learning model using at least one or more of medical images, patches, batches, and/or analysis results. The training may refer to a process of changing or updating weights associated with the machine learning model through one or more of forward propagation and backward propagation of the machine learning model by using at least one patch, batch and/or analysis result. In the present disclosure, "each of a plurality of A" may refer to each of all components included in the plurality of A, or may refer to each of some of the components included in a plurality of A. For example, each of a plurality of reference medical images may refer to each of all reference medical images included in a plurality of reference medical images, or to each of some reference medical images included in a plurality of reference medical images. Similarly, each of a plurality of patches may refer to each of all patches included in a plurality of patches, or may refer to each of some patches included in a plurality of patches.

In the present disclosure, the "analysis result" may include at least one of genetic information included in at least a partial region (e.g., patch, batch, and the like) of a medical image, characteristic or information of a specific protein, cell, tissue, and/or structure within the human body. The analysis result may refer to any characteristic or information of at least one patch included in the medical image, which may be inferred through the machine learning model. On the other hand, the ground truth data of the analysis result may be obtained as a result of the annotation by an annotator.

In the present disclosure, the "medical information" may refer to any medically meaningful information that can be extracted from the medical image, including, for example, regions, locations or sizes of tumor cells in the medical image, cancer diagnosis information, information associated with cancer risk of a patient, and/or medical conclusion associated with cancer treatment, or the like, but not limited thereto. In addition, the medical information may include not only quantified numerical values that can be obtained from the medical image, but also visualized information of the numerical values, prediction information according to the numerical values, image information, statistical information, or the like. The generated medical information may be provided to a user terminal, or output or transmitted to and displayed on a display device.

In the present disclosure, "spatial information of a medical image" may include information of a position corresponding to the pixel, the patch, and/or the batch in the medical image.

In the present disclosure, "statistical information of a medical image" may refer to any information that statistically indicates numerical values/distributions associated with objects (e.g., tumor cells, immune cells, and the like) included in the medical image, correlation between the objects included in the medical image, or the like.

In the present disclosure, "data" may refer to the medical image itself, information related to the medical image, the medical information, or a combination of the medical image and information.

FIG. 1 illustrates an example of outputting medical information 130 associated with a medical image 100 from the medical image 100. The medical image 100 may be an image of a tissue removed from the patient's body, may be captured or scanned by using a digital scanner, and may include information of specific proteins, cells, tissues and/or structures in the patient. Further, the medical information 130 associated with the medical image 100 may refer to any information associated with a patient that can be analyzed from the medical image 100, and may include information associated with at least one of normal cells, normal epithelium, normal stroma, tumor cell (or cancer cell), cancer epithelium, cancer stroma, immune cell (lymphocyte cell), necrosis, fat, and background, although not limited thereto.

An information processing system (not illustrated) may receive the medical image 100 and extract a plurality of patches (e.g., a patch 102) from the received medical image 100. Then, the information processing system may generate a plurality of batches 110_1 to 110_N (where N is a natural number greater than 1) including a plurality of extracted patches. In this case, the patch may be set to a predetermined size (e.g., a×b pixels, where a and b are natural numbers). Further, the size of the patch may be arbitrarily changed by user input. For example, the size of the patch may be set differently according to a specific protein, cell, tissue, structure, and the like which will be included in the medical information 130 to be extracted from the medical image 100.

The information processing system may derive an analysis result from the plurality of generated batches 110_1 to 110_N, and generate or output the medical information 130 based on the analysis result. That is, a plurality of operations for the plurality of batches 110_1 to 110_N may be performed to generate the medical information 130. In an example, the operations may include all graphic processing, computing processing, training of an artificial neural network model and/or inference using the artificial neural network model, which can be performed with respect to the medical image 100 and/or the plurality of batches 110_1 to 110_N. The analysis result and/or the medical information 130 may be output or provided to the user terminal (not illustrated) and displayed on the display device associated with the user terminal (e.g., the display device connected to the user terminal, or the like). Additionally or alternatively, the information processing system may output such analysis result and/or the medical information 130 to the display device included in or connected to the information processing system. Through the display device, the analysis result and/or the medical information 130 output by the information processing system may be provided to the user.

Generally, if the information processing system performs a plurality of operations for the plurality of batches 110_1 to 110_N, the plurality of operations may be serially performed by a single processor. Therefore, it may take a relatively long time to generate the medical information 130 from the medical image 100.

Conversely, a plurality of processors (e.g., CPU, accelerator or the like) of the information processing system may perform a plurality of operations, thereby performing the plurality of operations in parallel. Accordingly, the time required for generating the medical information 130 by the plurality of processors may be significantly shorter than the time required for generating the medical information 130 by a single processor. In addition, since a plurality of operations is distributed to each of a plurality of processors, the amount and/or time of work to be processed by one processor can also be reduced. This parallel processing will be described in detail below with reference to FIGS. 3A to 3C and 4.

Each of a plurality of patches extracted from the medical image may include spatial information on the medical image 100. For example, the patch may include data associated with a two-dimensional coordinate value on the medical image 100. In another example, the patch may include data for a unique identification number indicating a location of the patch on the medical image 100. Such spatial information may be used in the process of generating the batches 110_1 to 110_N. In addition, the information processing system may generate or output the medical information 130 based on the spatial information and the analysis result of a plurality of batches. For example, the spatial information on the medical image 100 may be used in the process of reconstructing a plurality of patches divided from the medical image 100 to generate the medical information 130. This will be described in detail below with reference to FIGS. 5 to 7.

The medical information 130 generated from the medical image 100 may include information of characteristics or types of a tissue and/or a cell corresponding to each pixel included in the medical image 100. The medical information 130 may further include color information corresponding to the characteristics or the types of the tissue and/or the cell. For example, the medical information 130 may include a cancer stroma tissue region 132 displayed in green and a cancer epithelial tissue region 134 displayed in blue. Further, the medical information 130 may include a region 136 indicating an empty space displayed in orange. Such medical information 130 may be output or provided to the user terminal and displayed on the display device connected to the user terminal, or displayed on the display device connected to the information processing system. The medical information may include information of any tissues and/or cells of a patient distinguished by any numbers and colors corresponding thereto. Additionally or alternatively, the medical information may include information of various graphic elements, such as any shapes, any texts or the like corresponding to the classified cells and/or tissues of the patient.

Figure 2:
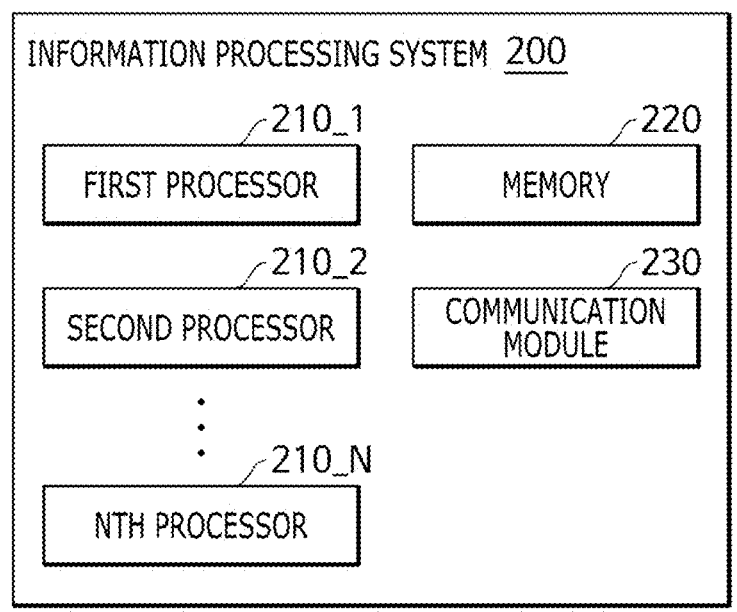
FIG. 2 illustrates an example of an information processing system for performing parallel processing of a medical image.

FIG. 2 illustrates an example of an information processing system 200 for performing parallel processing of a medical image. As illustrated, the information processing system 200 may include a plurality of processors 210_1, 210_2, . . . , 210_N (N is a natural number greater than 1), a memory 220 and a communication module 230. As illustrated in FIG. 2, the information processing system 200 may be configured to communicate information and/or data to an external device (e.g., the user terminal) using the communication module 230 via a network.

The memory 220 may include any non-transitory computer-readable recording medium. The memory 220 may include a permanent mass storage device such as random access memory (RAM), read only memory (ROM), disk drive, solid state drive (SSD), flash memory, and so on. In another example, a non-destructive mass storage device such as ROM, SSD, flash memory, disk drive, and so on may be included in the information processing system 200 as a separate permanent storage device that is distinct from the memory 220. Further, the memory 220 may store an operating system and at least one program code (e.g., a code for a program and/or application installed in the user terminal and providing a service related with the medical image).

These software components may be loaded from a computer-readable recording medium separate from the memory 220. Such a separate computer-readable recording medium may include a recording medium directly connectable to the information processing system 200, and may include a computer-readable recording medium such as a floppy drive, a disk, a tape, a DVD/CD-ROM drive, a memory card, and the like, for example. As another example, the software components may be loaded into the memory 220 through the communication modules rather than the computer-readable recording medium. For example, at least one program may be loaded into the memory 220 based on a computer program installed by the files provided by a developer or a file distribution system that distributes an installation file of an application via a network connected to the information processing system 200.

The plurality of processors 210_1 to 210_N may be configured to process instructions of the computer program by performing basic arithmetic, logic, and input and output operations. The plurality of processors 210_1 to 210_N may include two or more processors. The instructions may be provided to the plurality of processors 210_1 to 210_N by the memory 220 or the communication module 230. The plurality of processors 210_1 to 210_N may be configured to execute the received instructions according to a program code stored in a recording device such as the memory 220. For example, at least some of the plurality of processors 210_1 to 210_N may include an accelerator.

The communication module 230 may provide a configuration or a function for the information processing system 200 to communicate with the external device such as the user terminal and/or another system (e.g., a separate cloud system, and the like) via a network (not illustrated). For example, a request or data (e.g., a request to process medical image, a request to output medical information, and the like) generated according to a program code stored in the external device may be transmitted to the information processing system 200 via the network under the control of the communication module 230. Conversely, a control signal or instruction provided under the control of at least one of the plurality of processors 210_1 to 210_N of the information processing system 200 may be provided through the communication module 230 and network and received by the external device and/or another system via the communication module of the external device and/or another system.

Meanwhile, although not illustrated in FIG. 2, the information processing system 200 may further include an input and output interface (not illustrated). The input and output interface may be means for interfacing with an input or output device (not illustrated) that may be connected to, or included in the information processing system 200. For example, the input device may include a sensor such as a keyboard, a microphone, a mouse, an audio sensor, an image sensor, and the like, and the output device may include a device such as a display, a speaker, and the like. The input and output interface may be included in the information processing system 200 or may be configured as a separate device and connected to the information processing system 200 by wire or wirelessly. The information processing system 200 may include more components than those illustrated in FIG. 2. Meanwhile, most of the related components may not necessarily require exact illustration.

The plurality of processors 210_1 to 210_N of the information processing system 200 may be configured to manage, process, and/or store the information and/or data received from the external device and/or the external system. The information and/or data processed by the plurality of processors 210_1 to 210_N may be provided to the external device and/or the external system via a network connected to the communication module 230 and the information processing system 200. The plurality of processors 210_1 to 210_N of the information processing system 200 may receive a request for information for the processing of medical image from the external device and/or the external system via the network connected to the communication module 230 and the information processing system 200. The information processing system 200 may receive a plurality of medical images from an external memory via the network. The plurality of processors 210_1 to 210_N of the information processing system 200 may be configured to output the processed information and/or data through the output device such as a display output device (e.g., a touch screen, a display, and the like), an audio output device (e.g., a speaker), and the like, which may be included in the external device and/or the external system.

Each of the plurality of processors 210_1 to 210_N may be configured to process the operations for parallel processing of a medical image. In an example, at least some of the plurality of processors 210_1 to 210_N (i.e., the first processor) may perform the operation of extracting a set of patches from the image to generate a batch and providing the generated batch to a second processor. In an example, the first processor may refer to CPU, and the second processor may refer to one or more of the plurality of processors 210_1 to 210_N that do not process the operation described above. For example, it may refer to an accelerator for processing computation through the machine learning model. Specifically, the second processor may perform the operation of outputting an analysis result from the received batch using the machine learning model. The operation performed as described above may be stored in a storage medium or provided to another processor (e.g., the first processor or another processor) for generating medical information associated with the medical image based on analysis result.

The number of patches included in the batch generated by the first processor may be two or more. Using a batch including two or more patches for the training and/or inferring process of the machine learning model can provide much faster speed than using one patch. For example, if it is assumed that there are 1000 patches, inputting a batch including 100 patches into the machine learning model for ten times is faster than inputting these patches into the machine learning model one by one for 1000 times in terms of the total processing time taken to generate the analysis results for the batch by using an accelerator.

According to another example, when the machine learning model is implemented as a deep neural network, the statistical amount of a plurality of patches included in the batch may be used to train the machine learning model. For example, in the BatchNormalization layer, the statistical information such as an average vector and a variance vector may be extracted using a feature map in the intermediate stage, which is generated by inputting the batches included in the batch to the deep neural network. Such information can be used in the training of the machine learning model, thus greatly improving the performance of the machine learning model.

Figure 3A:
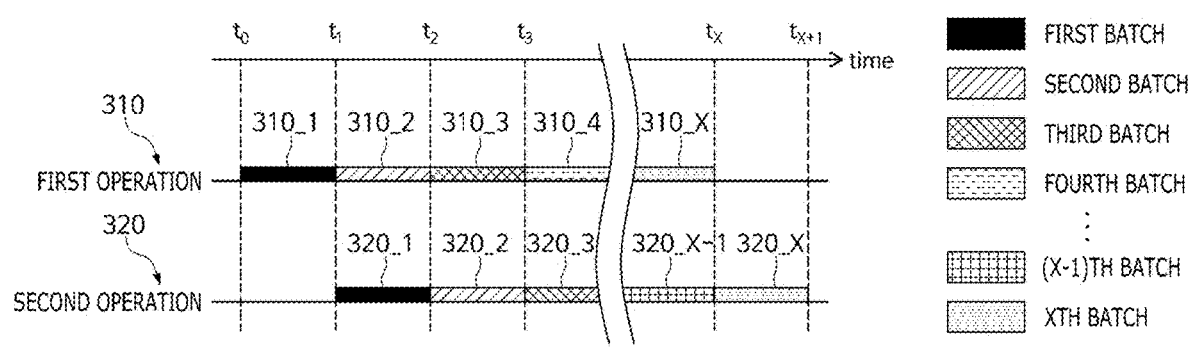
FIGS. 3A, 3B, and 3C illustrate an example of parallel processing a medical image using two processors.
Figure 3B:
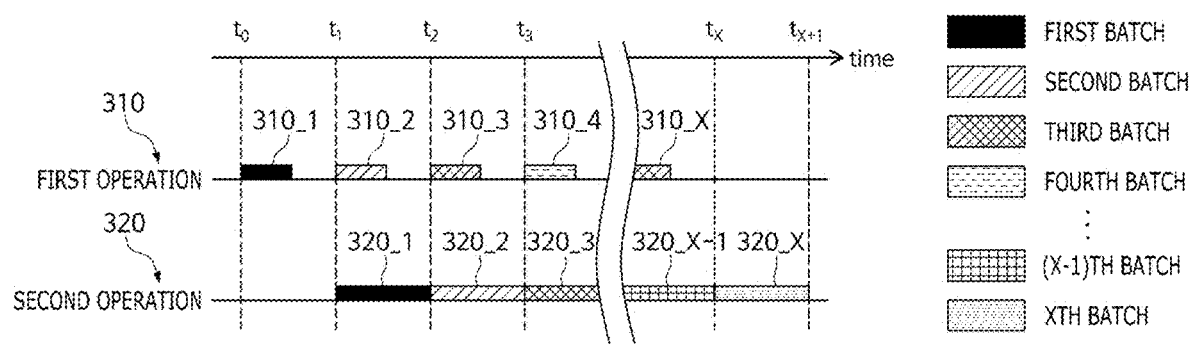
Figure 3C:
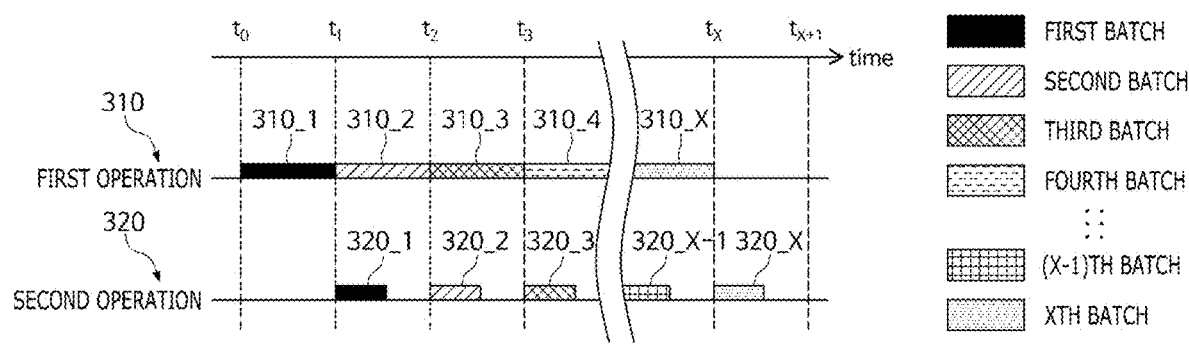

FIGS. 3A to 3C illustrate an example of parallel processing a medical image using two processors. As illustrated, X number of batches (X is a natural number of 2 or more) may be extracted from the medical image. Each batch may include a plurality of patches. In this case, X number of batches may be the batches extracted from one medical image, or the batches extracted from a plurality of medical images. In an example, the medical image may be stored in a memory accessible by the first processor (e.g., an internal memory of the information processing system or a memory included in the external device). While FIGS. 3A to 3C illustrate that six or more batches are extracted, aspects are not limited thereto. For example, one to five batches may be extracted from the medical image.

A first operation 310 and a second operation 320 may be performed by different processors. For example, the first operation 310 may be performed by the first processor (e.g., CPU, not illustrated), and the second operation 320 may be performed by the second processor (e.g., accelerator, not illustrated). Additionally, the first operation 310 and the second operation 320 may refer to different operations for the medical image. For example, the first operation 310 may include extracting a batch including a set of patches from the medical image and providing the extracted batch to the second processor. Additionally, the first operation 310 may include a preprocessing operation of the medical image. In an example, the pre-processing operation of the medical image may refer to any pre-processing operation that enhances quality of the medical image for the purpose of processing and analysis of the medical image, but aspects are not limited hereto, and it may refer to at least one of contrast adjustment, brightness adjustment, saturation, blur adjustment, noise injection, random crop, and sharpening.

The second operation 320 may perform an operation of outputting an analysis result for a corresponding batch from the received batch including a set of patches, by using the machine learning model. The second operation 320 may refer to any computation associated with the machine learning model for outputting the analysis result by using the received batch as input data.

If the machine learning model is trained by the second processor, the second operation 320 may include an operation of training the machine learning model by the second processor. To this end, the second processor may input each of a plurality of batches in a plurality of medical pathology images into the machine learning model, and receive an analysis result for each of a plurality of batches, for example. In this case, the second processor may calculate a loss by comparing the analysis result for each of a plurality of batches with the ground truth result (i.e., a plurality of reference analysis results) of the batch corresponding to each of a plurality of batches, and perform back-propagation of the calculated loss with the machine learning model so as to train the machine learning model. According to another example, if the second processor performs a validation operation of the machine learning model or a prediction operation through the machine learning, the second operation 320 may include an operation of outputting an analysis result corresponding to each of one or more batches through the machine learning model. In addition, the second operation 320 may include an operation of generating medical information based on the output analysis result. The result of the second operation processed as described above may be provided to the storage medium and/or the first processor.

The first processor may collect the analysis results for a plurality of batches, and generate medical information associated with the medical image based on the collected analysis results. Alternatively, at least a part of the operation of generating such medical information may be performed by the second processor or by a processor other than the first processor and the second processor. For example, it is possible to prevent one processor from computational overloads by having the first processor perform the operation of collecting the analysis result and having the second processor perform the operation of performing additional computation from the analysis result.

In an example, each of a plurality of patches included in or associated with a plurality of batches may include spatial information on the medical image (e.g., information indicating position in the medical image). The first processor may generate a processed image based on the spatial information of each of a plurality of patches. In an example, the processed image may refer to an image reconstructed by dividing the received medical images in the units of batches and then combining the divided batches. Medical information associated with the medical image may be generated based on the first analysis result, the second analysis result, and the processed image. In an example, the generated medical information may be included in the processed image. That is, the processed or reconstructed image may be an image restored by combining the analysis results corresponding to the patches or batches.

FIG. 3A is a first example of parallel processing a medical image. From $t_0$ to $t_1$, the first processor may perform a first operation 310_1 for a first batch, by extracting a first set of patches from one or more medical images to generate the first batch, and providing the generated first batch to the second processor. From $t_1$ to $t_2$, the first processor may perform a first operation 310_2 for a second batch, by extracting a second set of patches from one or more medical images to generate the second batch, and providing the generated second batch to the second processor. Further, from $t_1$ to $t_2$, the second processor may perform a second operation 320_1 for the first batch, by outputting a first analysis result using the first batch received from the first processor. That is, from $t_1$ to $t_2$, while the first processor is performing the first operation 310_2 for the second batch, the second processor may perform the second operation 320_1 for the first batch. The second operation may include an operation of storing the output analysis result in the storage medium.

Accordingly, the time frame for the first operation 310_2 for the second batch may overlap with the time frame for the second operation 320_1 for the first batch performed by the second processor. That is, while the first processor is performing the first operation 310_2 for the second batch, the second processor may process the second operation 320_1 for the first batch in parallel. While the first processor is performing the first operation 310_2 for the second batch, at least a part of the second operation 320_1 for the first batch of the second processor may be performed. Likewise, the time frame for the first operation 310_3 for a third batch may overlap with the time frame for the second operation 320_2 for the second batch performed by the second processor, and the time frame for the first operation 310_4 for the fourth batch may overlap with the time frame for the second operation 320_3 for the third batch performed by the second processor. That is, from $t_{X-1}$ to $t_X$, the first processor may perform the first operation 310_X for an Xth batch, by extracting an Xth set of patches from the one or more medical images to generate the Xth batch, and providing the generated Xth batch to the second processor. Further, from $t_{X-1}$ to $t_X$, the second processor may perform the second operation 320_X-1 for an (X-1)th batch, by outputting an (X-1)th analysis result by using the (X-1)th batch received from the first processor. That is, from $t_{X-1}$ to $t_X$, while the first processor is performing the first operation 310_X for the Xth batch, the second processor may perform the second operation 320_X-1 for the (X-1)th batch in parallel. Accordingly, the time frame for the first operation 310_X of the Xth batch may overlap with the time frame for the second operation 320_X-1 for the (X-1)th batch performed by the second processor.

From $t_X$ to $t_{X+1}$, the first processor may not perform any operation. Further, from $t_X$ to $t_{X+1}$, the second processor may perform the second operation 320_X for the Xth batch, by outputting the Xth analysis result by using the Xth batch received from the first processor. Additionally, after $t_{X+1}$, the first processor and/or another processor (e.g., the second processor, or a processor other than the first processor and the second processor) may further perform the operation of generating medical information by using the first to Xth analysis results extracted between $t_1$ and $t_{X+1}$. In an example, the medical information may include not only quantified numerical values that can be obtained from the medical image, but also visualized information of the numerical values, prediction information according to the numerical values, image information, statistical information, or the like. For example, the first processor and/or another processor may generate such medical information by using the machine learning model that is trained to infer the medical information based on one or more analysis results. As another example, the second processor may be configured to generate the medical information by using the first to Xth analysis results.

According to another example, the first processor and/or another processor may start the operation of receiving the analysis result for some of all batches from the second processor, and using the received analysis results for some batches to generate the medical information associated with the medical image. Such operation may be finished after the analysis results for the remaining batches are received and the received analysis results for the remaining batches are reflected in the medical information.

FIG. 3B is a second example of parallel processing a medical image. As illustrated, the time taken for the first operation 310 for one batch may be shorter than the time taken for the second operation 320 for one batch. In FIG. 3B, the configuration already described above or overlapping with FIG. 3A will not be described.

From $t_{X-1}$ to $t_X$, the first processor may perform a first operation 310_X for an Xth batch, by extracting an Xth set of patches from one or more medical images to generate the Xth batch, and providing the generated Xth batch to the second processor. In this case, the first operation 310_X for the Xth batch is illustrated as starting at $t_{X-1}$ and ending before $t_X$, but aspects are not limited thereto. For example, the first operation 310_X for the Xth batch may be performed at any time between $t_{X-1}$ and $t_X$. Meanwhile, from $t_{X-1}$ to $t_X$, the second processor may perform a second operation 320_X-1 for an (X-1)th batch, by outputting an (X-1)th analysis result by using the (X-1)th batch received from the first processor. That is, from $t_{X-1}$ to $t_X$, while the first processor is performing the first operation 310_X for the Xth batch, the second processor may perform the second operation 320_X-1 for the (X-1)th batch in parallel. Accordingly, the time frame for the first operation 310_X of the Xth batch performed by the first processor may overlap with at least a part of the time frame for the second operation 320_X-1 of the (X-1)th batch performed by the second processor.

FIG. 3C is a third example of parallel processing a medical image. As illustrated, the time taken for the first operation 310 for one batch may be longer than the time taken for the second operation 320 for one batch. In FIG. 3C, the configuration already described above or overlapping with FIG. 3A will not be described.

From $t_{X-1}$ to $t_X$, the first processor may perform a first operation 310_X for an Xth batch, by extracting an Xth set of patches from one or more medical images to generate the Xth batch, and providing the generated Xth batch to the second processor. Meanwhile, from $t_{X-1}$ to $t_X$, the second processor may perform a second operation 320_X-1 for an (X−1)th batch, by outputting an (X−1)th analysis result by using the (X−1)th batch received from the first processor. In an example, while the second operation 320_X−1 for the (X−1)th batch is illustrated as starting at $t_{X-1}$ and ending before $t_X$, aspects are not limited thereto. For example, the second operation 320_X−1 for the (X−1)th batch may be performed at any time between $t_{X-1}$ and $t_X$. That is, from $t_{X-1}$ to $t_X$, while the first processor is performing the first operation 310_X for the Xth batch, the second processor may perform the second operation 320_X−1 for the (X−1)th batch. Accordingly, at least a part of the time frame for the second operation 320_X−1 for the (X−1)th batch performed by the second processor may overlap with the time frame for the first operation 310_X for the Xth batch performed by the first processor.

Figure 4:
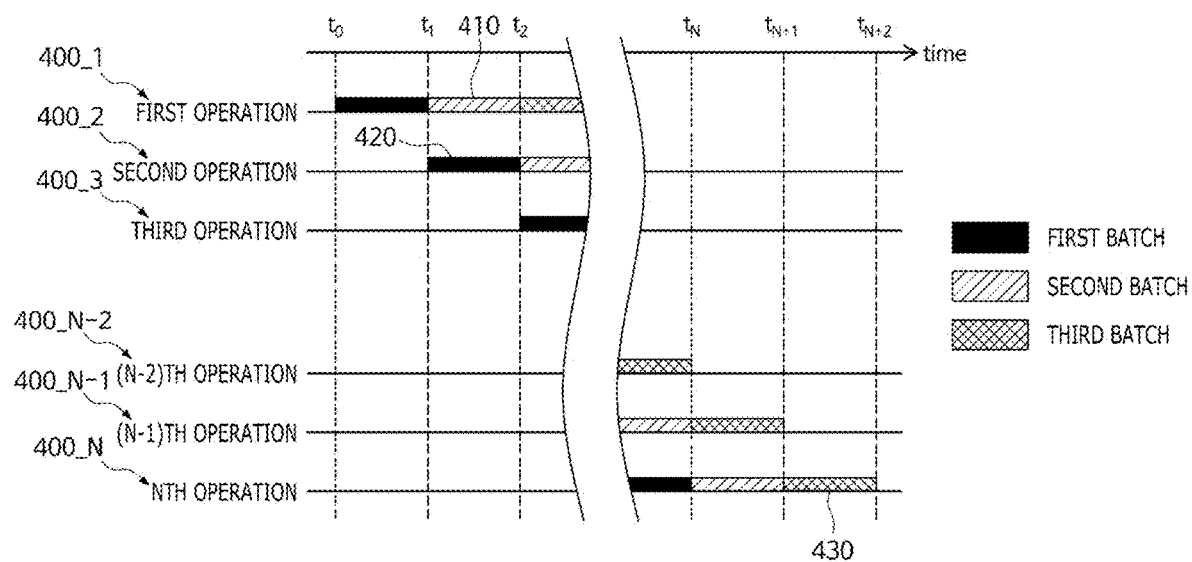
FIG. 4 illustrates an example of parallel processing a medical image using N number of processors.

FIG. 4 illustrates an example of parallel processing a medical image using N number of processors. In an example, the method for processing a medical image may be divided into N number of operations. For example, if the method for processing a medical image includes a plurality of processing steps, the N number of operations may include successive processing steps in groups. For example, a first operation 400_1 may include first and second steps, a second operation 400_2 may include a third step, a third operation 400_3 may include a fourth step, an (N−2)th operation 400_N−2 may include fifth and sixth steps, an (N−1)th operation 400_N−1 may include seventh and eighth steps, and N operations may refer to ninth to Jth steps (where, J is a natural number greater than 9). That is, any one operation may include one or more continuous processing steps.

As illustrated, the method for extracting one batch and processing the extracted batch may be divided into N number of operations. For example, the operation of extracting one set of patches from one or more medical images to generate a batch and providing the generated batch to the second processor may be included in the first operation performed by the first processor. The operation of deriving an analysis result from the batch generated by using the machine learning may be divided into (N−1) number of operations performed by (N−1) number of processors. Meanwhile, for convenience of explanation, FIG. 4 illustrates an example in which three batches are extracted from the medical image and processed, but aspects are not limited thereto. For example, one, two, or four or more batches may be extracted from the medical image. Unlike FIG. 4, the first operation of extracting one set of patches from one or more medical images to generate a batch and providing the generated batch to the second processor may be divided into several sub-operations and assigned to several processors.

As illustrated, from $t_1$ to $t_2$, the first processor may perform a first operation 410 of generating a second batch. Further, from $t_1$ to $t_2$, the second processor may perform a second operation 420 which is a part of the operation of outputting the first analysis result by using the first batch received from the first processor. That is, from $t_1$ to $t_2$, while the first processor is performing the first operation 410 for the second batch, the second processor may perform the second operation 420 for the first batch. Accordingly, at least a part of the time frame for the first operation 410 for the second batch may overlap with at least a part of the time frame for the second operation 420 for the first batch performed by the second processor. Additionally, the remaining operation of outputting the first analysis result by using the first batch may be performed by a plurality of processors (N−2 number of processors) different from the first processor and the second processor. According to such process, from $t_{N+1}$ to $t_{N+2}$, the Nth processor may perform an Nth operation 430 for a third batch. In the present disclosure, it is assumed that the number of processors, that is, N is 6 or more for convenience of illustration, but aspects are not limited, and N may be any natural number equal to or less than 5.

According to another example, one processor may be configured to perform the extracting and the analyzing operations for one batch. For example, a batch at a specific time point may be referred to as Y (where, Y is a natural number), and another batch at the next time point may be referred to as (Y+1). If an Nth operation for a Y batch is being performed by the Nth processor (where, N is the number of processors involved in the processing) at a specific time point, the (N−1)th processor may perform an (N−1)th operation for a (Y+1) batch at the same time. Further, at the same time point, the (N−2)th processor may perform an (N−2)th operation for a (Y+2) batch. Likewise, at the same time point, the first processor may simultaneously perform the first operation for the (Y+N−1) patch. In the present disclosure, although it is explained that one processor performs the extracting and the analyzing operations for one batch, aspects are not limited thereto, and two or more processors may be configured to perform the extracting and the analyzing operations for one batch.

According to another example, the operation of extracting and processing each of a plurality of batches from a medical image may be divided into N number of operations. Each of a plurality of operations 400_1 to 400_N may include at least some of operations of receiving a medical image from the memory (e.g., memory 220), extracting a patch (or a batch) from the medical image, pre-processing (e.g., contrast adjustment, brightness adjustment, saturation adjustment, blur adjustment, noise injection, random crop and/or sharpening, and the like), designing and training a machine learning model and/or inferring with the machine learning model, by using a data set including the extracted patch (or batch), reconstructing the patch (or batch), or generating medical information associated with the medical image based on the analysis results. That is, at least some of a series of operations for analyzing the medical image may be grouped and assigned as one operation. The one operation assigned as described above may be assigned to one of a plurality of processors and performed at a specific time point, and at such specific time point, parallel processing may be performed, that is, another operation may be performed in another processor.

As described above, the information processing system according to various examples uses a plurality of processors to extract a plurality of patches from at least one medical image and train an artificial neural network model based on the extracted patches, or extract a plurality of patches from at least one medical image and infer the medical information from the artificial neural network model by using the extracted patches as inputs.

Figure 5:
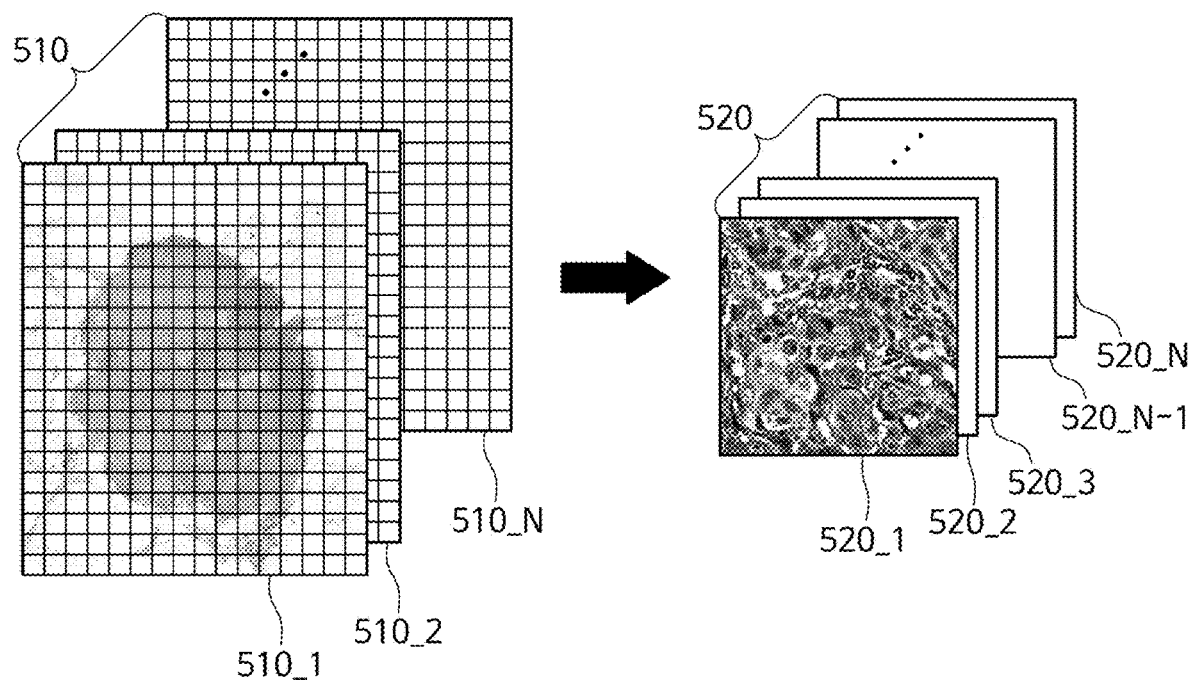
FIG. 5 illustrates an example of generating a training batch by extracting a set of training patches from a plurality of reference medical images.

FIG. 5 is a view for explaining a method in which the information processing system extracts a plurality of patches from at least one medical image by using a plurality of processors and trains an artificial neural network model based on the extracted patches.

FIG. 5 illustrates an example of extracting a set of training patches 520_1 to 520_N (N is a natural number equal to or greater than 2) from a plurality of reference medical images 510 to generate a training batch 520. At least one of first to Mth processors 210_1 to 210_M (where, M is a natural number equal to or greater than 2) may train the machine learning model so as to infer the reference analysis result by using the training batch 520. Meanwhile, in the above disclosure, the terms are unified as "medical image", "patch" and "batch", but in FIGS. 5 to 8, they are further separated and used. Specifically, "reference medical image", "training patch" and "training batch" may refer to data used for the training of the machine learning model, and "medical image", "patch" and "batch" may refer to data used for the inference of the machine learning model. However, the aspects are not limited thereto, and each of "reference medical image", "training patch", and "training batch" may be replaced and construed as "medical image", "patch" and "batch". In addition, each of "medical image", "patch", and "batch" may be replaced and construed as "reference medical image", "training patch", and "training batch".

The processor may perform segmentation for a specific object in each of the plurality of reference medical images 510. For example, the processor may perform segmentation for at least one of the objects of a tumor cell (or cancer cell), a cancer epithelial, a cancer stroma, and a lymphocyte cell. The processor may extract the set of training patches 520_1 to 520_N including the corresponding specific object to generate the training batch 520. Additionally or alternatively, the processor may extract the set of training patches 520_1 to 520_N that do not include the specific object to generate a training batch (not illustrated). With such configuration, the processor may improve performance of the machine learning model to infer an analysis result associated with the specific object. Additionally or alternatively, the processor may receive a reference medical image having segmentation information for a specific object in the reference medical image, and extract training patches including the specific object by using the reference medical image, to thus generate a training batch.

The processor may generate a training batch by extracting the patches in each of the first to Nth reference medical images 510_1 to 510_N based on the spatial information of the first to Nth reference medical images 510_1 to 510_N. From each of the first to Nth reference medical images 510_1 to 510_N, a patch located at a first point (e.g., an area including one or more pixels) may be extracted to generate the training batch 520. For example, the first training patch 520_1 may be extracted from a first point of the first reference medical image 510_1, and the second training patch 520_2 may be extracted from a first point of the second reference medical image 510_2 corresponding to the first point of the first reference medical image 510_1, and the Nth training patch 520_N may be extracted from a first point of the Nth reference medical image 510_N corresponding to the first point of the first reference medical image 510_1. Additionally, the processor may further generate a training batch (not illustrated) by extracting a patch located at a second point from each of the first to Nth reference medical images 510_1 to 510_N based on the spatial information of the first to Nth reference medical images 510_1 to 510_N. In this case, the second point may be determined based on the first point. For example, the second point may be determined to be the same as, or adjacent to the first point. In another example, the second point may be determined to be a point separated by a predetermined distance in a predetermined direction from the first point. With this configuration, the processor can simplify the calculation for reconstructing the extracted patches to generate medical information.

Figure 6:
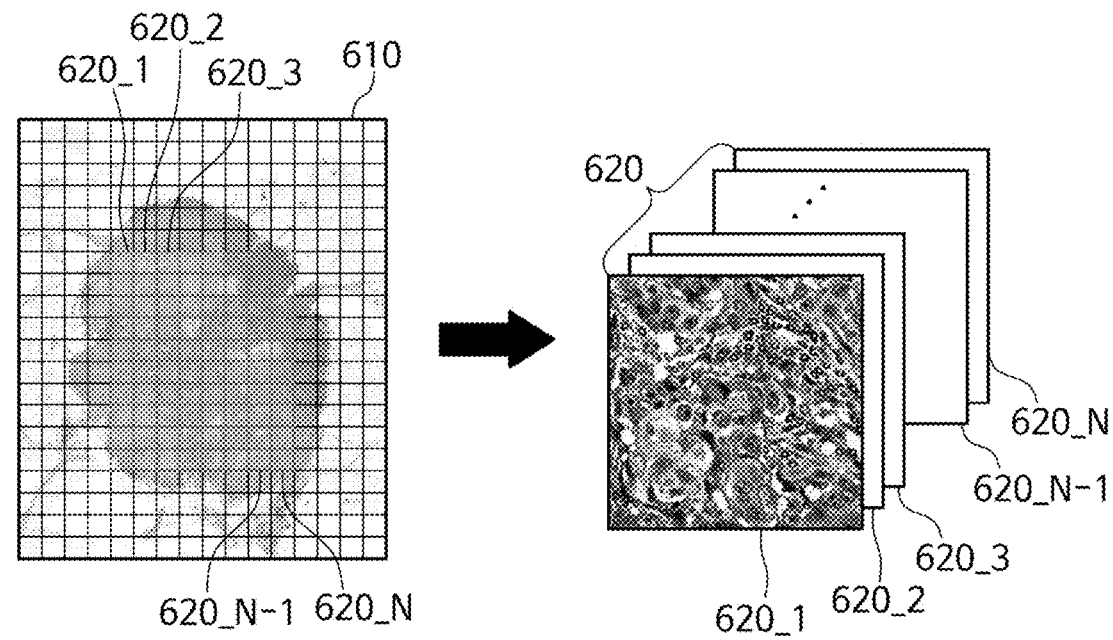
FIG. 6 illustrates an example of generating a batch by extracting a set of patches from one medical image.

FIG. 6 is a view illustrating a method in which the information processing system extracts a plurality of patches from at least one medical image by using a plurality of processors and receives medical information from an artificial neural network model by inputting the extracted patches.

FIG. 6 illustrates an example of generating a batch 620 by extracting a set of patches 620_1 to 620_N (where, N is a natural number equal to or greater than 2) from one medical image 610. The processor may extract the first patch 620_1 from the medical image 610 to generate a batch 620. Then, the processor may extract a second patch 620_2 from the medical image 610 based on the spatial information on the medical image 610 of the first patch 620_1. Likewise, the processor may extract a third patch 620_3 from the medical image 610 based on the spatial information on the medical image 610 of the second patch 620_2. Likewise, the processor may extract the Nth patch 620_N from the medical image 610 based on the spatial information on the medical image 610 of the (N−1)th patch 620_N−1. For example, the (N−1)th patch 620_N−1 and the Nth patch 620_N may be adjacent to each other in the medical image 610. Additionally, at least a part of the (N−1)th patch 620_N−1 and at least a part of the Nth patch 620_N may overlap with each other in the medical image 610. As illustrated in FIG. 6, the batch 620 may include adjacent patches in the medical image 610, but aspects are not limited thereto. The batch 620 may include a plurality of patches which are spatially randomly extracted from the medical image 610. The generated batch 620 may be used as input data in the process of inference using the machine learning model.

Figure 7:
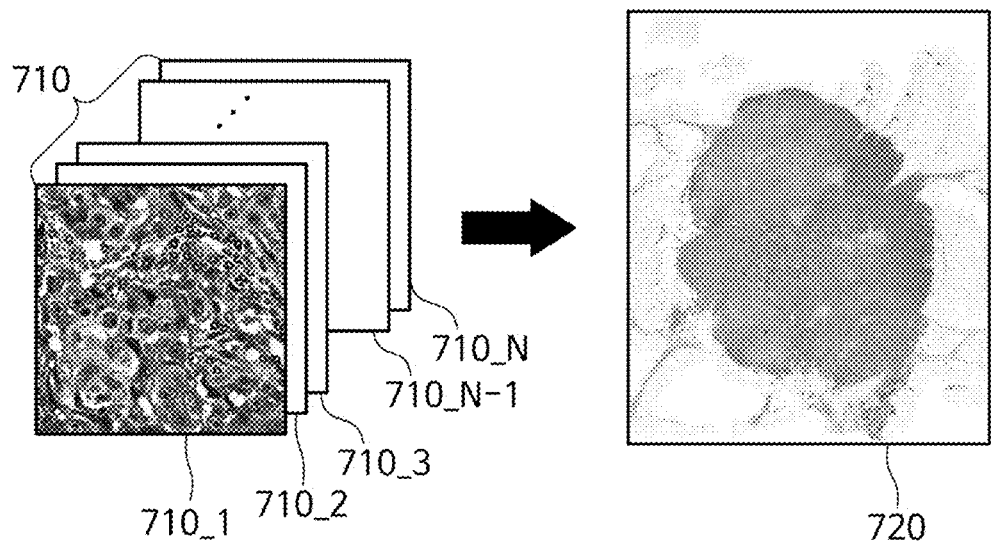
FIG. 7 illustrates an example of reconstructing an image using one batch.

FIG. 7 illustrates an example of reconstructing a processed image 720 by using one batch 710. As described above, an analysis result may be output from a set of patches 710_1 to 710_N (where N is a natural number equal to or greater than 2) extracted from one or more medical images. The processor may reconstruct the image 720 based on the analysis result extracted from the batch 710. Accordingly, reconstructing the image 720 based on the analysis result may refer to generating a processed image by recombining the set of patches 710_1 to 710_N. Also, reconstructing the image 720 based on the analysis result may refer to generating the medical information based on the processed image and the analysis result. For example, the medical information may be provided to a user in a visualized form.

The set of patches 710_1 to 710_N included in the batch 710 may include spatial information on the medical image. For example, each of a plurality of patches included in the set of patches 710_1 to 710_N may include a two-dimensional coordinate value on the medical image. The processor may reconstruct the image 720 based on the spatial information of the set of patches 710_1 to 710_N. The reconstructed image 720 may include the analysis result and/or the medical information generated based on the analysis result.

Meanwhile, although FIG. 7 illustrates that one image 720 is reconstructed from one batch 710 for convenience of description, aspects are not limited thereto. For example, the processor may reconstruct one medical image from a plurality of batches. As another example, the processor may reconstruct a plurality of medical images from a plurality of batches. In this case, each of a plurality of patches included in the batch may include spatial information including information of the medical image to which each patch belongs, and a two-dimensional coordinate value in the corresponding medical image.

Figure 8:
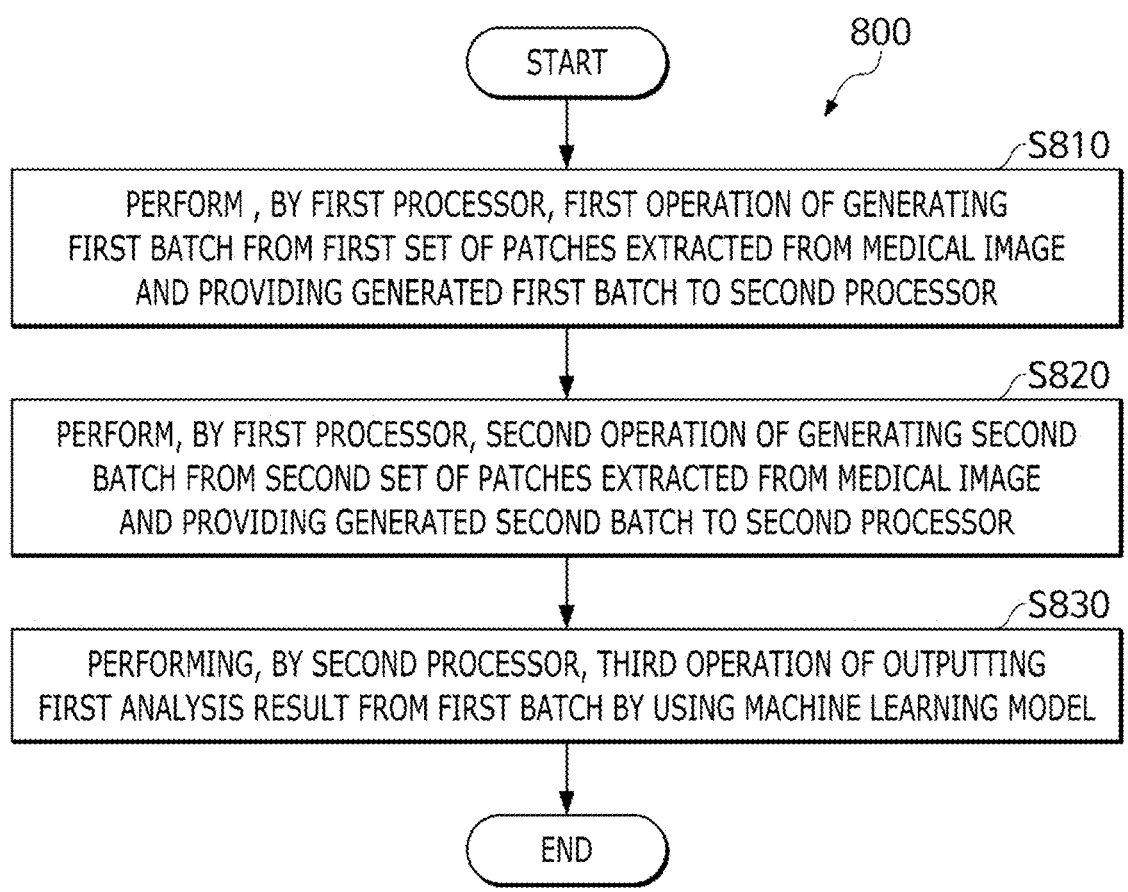
FIG. 8 illustrates an example of a method for parallel processing a medical image.

FIG. 8 illustrates an example of a method 800 for processing a medical image in parallel. The method 800 may be performed by at least some of the plurality of processors (e.g., the plurality of processors 210_1 to 210_N) illustrated in FIG. 2 of the information processing system.

The first processor of the information processing system may perform a first operation of generating a first batch from a first set of patches extracted from the medical image and providing the generated first batch to the second processor (S810). The medical image may be received from an internal or external memory of the information processing system. For example, the medical image may include a digitally scanned pathology image, an X-ray image, a CT image, or an MRI image. The first processor may perform a second operation of generating a second batch from a second set of patches extracted from the medical image (S820). In an example, each of the first set of patches and the second set of patches may include one or more patches. Further, each of the first batch and the second batch may include a first training batch and a second training batch used in a training process of the machine learning model and extracted from one or more reference medical images. In an example, the reference medical image may include a digitally scanned reference pathology image.

The medical image may include a plurality of reference medical images including a first reference medical image and a second reference medical image. The first processor may generate one batch by using the patches extracted from a plurality of reference medical images. For example, the first processor may extract x number of patches from the first reference medical image, extract y number of patches from the second reference medical image, extract z number of patches from the third reference medical image, and generate one batch including (x+y+z) number of patches. In an example, each of x, y, and z may be any of natural numbers.

The first processor may receive the digitally scanned pathology image including segmentation information of a specific object in the digitally scanned pathology image. In this case, the first processor may extract a first set of patches including the specific object and generate a first batch including the extracted first set of patches. The first processor may extract a second set of patches that do not include the specific object, and generate a second batch including the extracted second set of patches. According to another example, the first processor may extract a second set of patches including the specific object, and generate a second batch including the extracted second set of patches.

If the specific object is a cancer cell or cancer tissue, in the training process of the machine learning model, the first processor may extract the training patches so that the number of patches included in the first set of training patches including the cancer cell or cancer tissue, and the number of patches included in the second set of training patches that do not include the cancer cell or cancer tissue correspond to a predetermined number. For example, the number of training data may be properly adjusted, as the first processor extracts 50 patches for the first set of training patches including the cancer cell or cancer tissue, and extracts 50 patches for the second set of training patches that do not include the cancer cell or cancer tissue. As another example, if an area including cancer cell or cancer tissue in one or more reference medical images is insufficient to be used as the training data, the first processor may configure a batch by oversampling the patch including the cancer cell or cancer tissue. As another example, if a patch of a normal cell or tissue is extracted as the training patch to be included in the first batch and/or the second batch, the first processor may extract patches of a cancer cell or cancer tissue as the subsequent training patch. According to the method described above, by properly distributing the training data including a specific object and the training data that does not include the specific object, the machine learning model can be effectively trained.

The first set of patches belonging to the first batch and the second set of patches belonging to the second batch may be spatially associated with each other in the medical image. For example, each of at least one patch included in the first set of patches and each of at least one patch included in the second set of patches may be adjacent to each other or overlap with each other at least in part in the medical image. As another example, the first processor may extract the patches spaced apart at intervals in the medical image as the first set of patches and the second set of patches. In another embodiment, the first processor may randomly extract the first set of patches and the second set of patches from the medical image.

The second processor of the information processing system may perform a third operation of outputting the first analysis result from the first batch by using the machine learning model (S830). In this case, at least a part of the time frame for the second operation performed by the first processor may overlap with at least a part of the time frame for the third operation performed by the second processor.

The second processor may perform a fourth operation of outputting the second analysis result from the second batch by using the machine learning model. The first processor and/or another processor (i.e., a processor other than the first processor and the second processor) may generate medical information associated with the medical image based on the first analysis result and the second analysis result. While it is described herein that the medical information is generated based on the analysis results of two batches, aspects are not limited thereto, and the medical information may be generated based on the analysis results of three or more batches. In an example, the medical image may include a plurality of reference medical images used for the training process of the machine learning model.

The machine learning model may be trained by using a plurality of batches and a plurality of reference analysis results in the plurality of reference medical pathology images. The second processor may input each of a plurality of batches in a plurality of reference medical pathology images into the machine learning model, and receive an analysis result for each of a plurality of batches. In this case, the second processor may calculate a loss by comparing the analysis result for each of a plurality of batches with the ground truth result (i.e., a plurality of reference analysis results) of the batch corresponding to each of a plurality of batches, and perform back-propagation of the calculated loss with the machine learning model so as to train the machine learning model. Additionally or alternatively, such training process may be performed by the first processor. As described above, a plurality of reference medical pathology images may be used for the training process of the machine learning model, but the machine learning model may be trained by using one reference medical pathology image.

Each of a plurality of patches associated with the first batch and the second patch may include spatial information on the received reference medical image. A processed image may be generated based on the spatial information of each of a plurality of patches. Generating the processed image may be performed by the first processor and/or another processor. Medical information associated with the medical image may be generated based on the first analysis result, the second analysis result, and the processed medical image. Generating such medical information may be performed by the first processor and/or another processor. In an example, the medical information may include statistical information of the medical image.

The first processor may perform image processing on the generated first batch, and perform image processing on the generated second batch. In this case, the image processing on the first batch and the image processing on the second batch may include at least one of contrast adjustment, brightness adjustment, saturation adjustment, blur adjustment, noise injection, random cropping, or sharpening.

Figure 9:
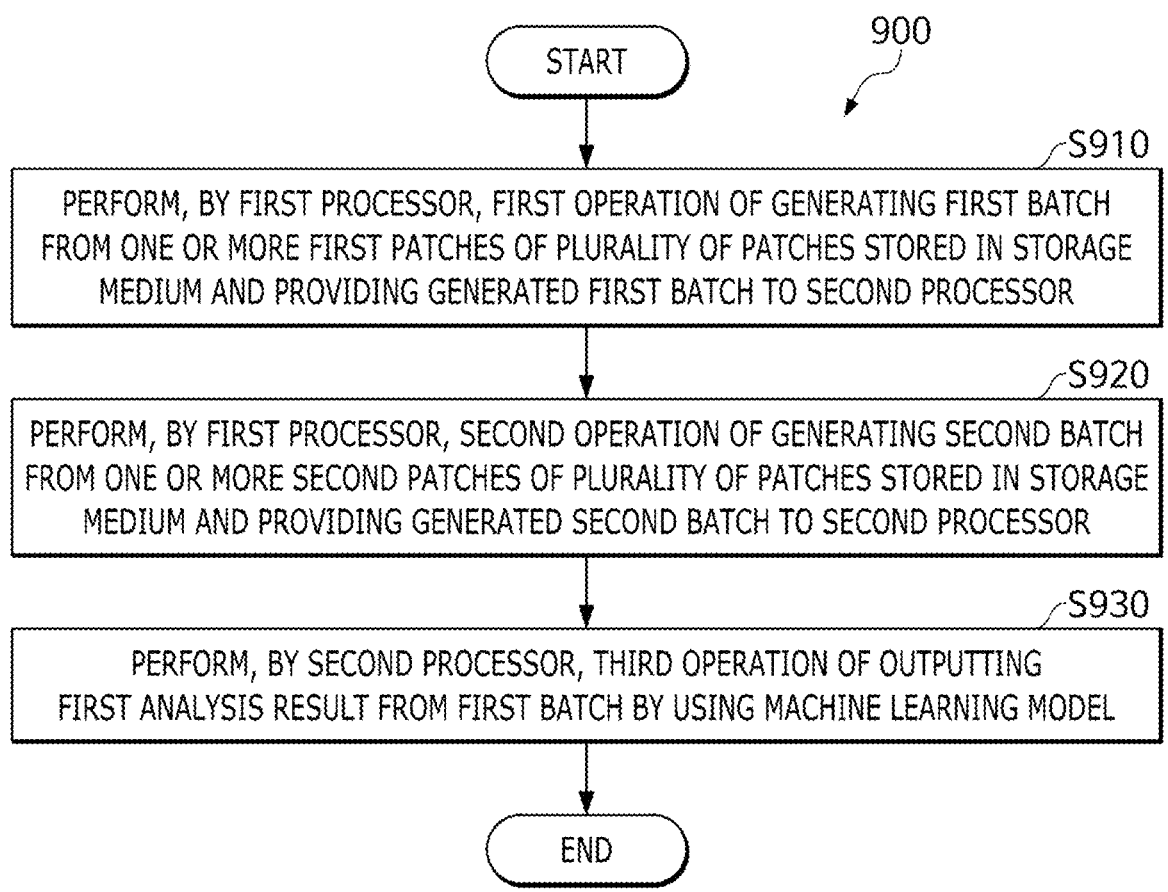
FIG. 9 illustrates another example of a method for parallel processing a medical image.

FIG. 9 illustrates another example of a method 900 for parallel processing a medical image. The method 900 may be performed by at least some of the plurality of processors (e.g., the plurality of processors 210_1 to 210_N) illustrated in FIG. 2. In FIG. 9, the configuration already described above or overlapping with FIG. 8 will not be described.

The first processor may perform a first operation of generating a first batch from one or more first patches of a plurality of patches stored in the storage medium and providing the generated first batch to the second processor (S910). Further, the first processor may perform a second operation of generating a second batch from one or more second patches of a plurality of patches stored in the storage medium and providing the generated second batch to the second processor (S920). In an example, a plurality of patches may be extracted in advance and stored in a storage medium independently of inference or training step of the machine learning model.

A plurality of patches stored in the storage medium may be extracted from the medical image. In an example, a subject that extracts a plurality of patches from the medical image may be the first processor, the second processor, another processor (a processor other than the first processor and the second processor in the information processing system), a processor included in a device separate from the information processing system and/or any combination of such processors. Further, the storage medium may be any storage medium included in the information processing system. Additionally or alternatively, the storage medium may be any storage medium that is accessible by, or coupled to the information processing system. For example, the storage medium may be a mass storage of a server device connected to the information processing system via the network, a cloud system, and/or the external device.

Further, the second processor may perform a third operation of outputting the first analysis result from the first batch by using the machine learning model (S930). In this case, at least a part of the time frame for the second operation performed by the first processor may overlap with at least a part of the time frame for the third operation performed by the second processor.

Figure 10:
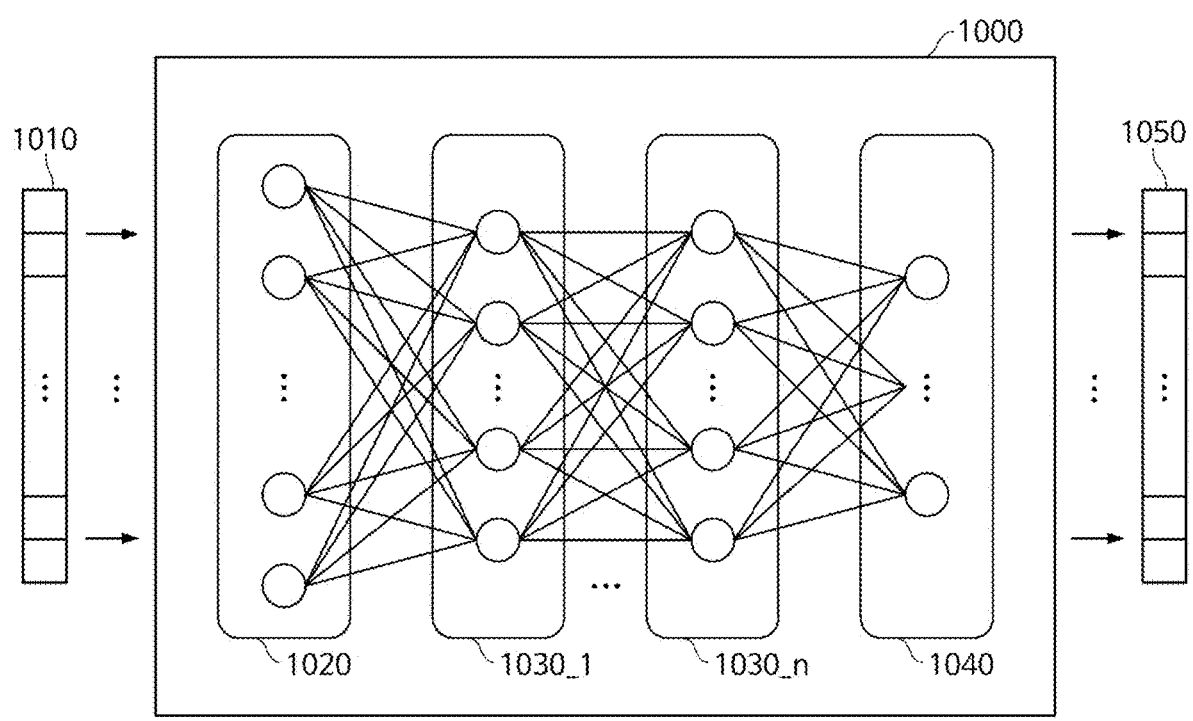
FIG. 10 is a structural diagram illustrating an artificial neural network model.

FIG. 10 is a structural diagram illustrating an artificial neural network model 1000. The machine learning model described above may refer to the artificial neural network model 1000. In the machine learning technology and cognitive science, the artificial neural network model 1000 refers to a statistical training algorithm implemented based on a structure of a biological neural network, or to a structure that executes such algorithm.

The artificial neural network model 1000 may represent a machine learning model that acquires a problem solving ability by repeatedly adjusting the weights of synapses by the nodes that are artificial neurons forming the network through synaptic combinations as in the biological neural networks, thus training to reduce errors between a target output corresponding to a specific input and a deduced output. For example, an artificial neural network model 700 may include any probability model, neural network model, and the like, that is used in artificial intelligence learning methods such as machine learning and deep learning.

The artificial neural network model 1000 may be implemented as a multi-layer perceptron (MLP) formed of multi-layer nodes and connections between them. The artificial neural network model 1000 may be implemented using one of various artificial neural network structures including the MLP. As illustrated in FIG. 10, the artificial neural network model 1000 may include an input layer 1020 receiving an input signal or data 1010 from the outside, an output layer 1040 outputting an output signal or data 1050 corresponding to the input data, and n number of hidden layers 1030_1 to 1030_$n$ positioned between the input layer 1020 and the output layer 1040 to receive a signal from the input layer 1020, extract the characteristics, and transmit the characteristics to the output layer 1040. In an example, the output layer 1040 may receive signals from the hidden layers 1030_1 to 1030_$n$ and output them to the outside.

The method of training the artificial neural network model 1000 includes the supervised learning that trains to optimize for solving a problem with inputs of teacher signals (correct answers), and the unsupervised learning that does not require a teacher signal. The method for parallel processing a medical image may use supervised learning, unsupervised learning, and/or semi-supervised learning to train the artificial neural network model 1000 configured to output the analysis result from one or more batches in the medical image. According to another example, the artificial neural network model 1000 for outputting medical information associated with the medical image may be trained based on a plurality of analysis results output from a plurality of batches in the medical image. The artificial neural network model 1000 trained in this way may output an analysis result and/or medical information of a patient related to a corresponding medical image.

As illustrated in FIG. 10, an input variable of the artificial neural network model 1000 that is capable of outputting an analysis result may be a vector 1010 indicating a batch including one set of patches extracted from the medical image, which includes one vector data element of the medical image. Under this configuration, the output variable may include a result vector 1050 indicating the analysis result for the input batch.

According to another example, the artificial neural network model 1000 may be trained to generate medical information according to the input variable. For example, the input variable may be the vector 1010 including vector data elements representing a plurality of analysis results for a plurality of batches included in the medical image. Under this configuration, the output variable may be configured as the result vector 1050 indicating the medical information associated with the medical image.

As described above, by matching the input layer 1020 and the output layer 1040 of the artificial neural network model 1000 with a plurality of input variables and a plurality of corresponding output variables, respectively, and adjusting synaptic values between nodes included in the input layer 1020, the hidden layer 1030_1 . . . 1030_$n$ (where n is a natural number equal to or greater than 2), and the output layer 1040, the artificial neural network model 1000 may be trained to infer the correct output corresponding to a specific input. For the inference of a correct output, the correct answer data of the analysis result may be used, and such correct answer data may be obtained as a result of annotation by an annotator. Through this training process, the features hidden in the input variables of the artificial neural network model 1000 can be confirmed, and the synaptic values (or weights) between the nodes of the artificial neural network model 1000 can be adjusted so that there can be a reduced error between the target output and the output variable calculated based on the input variable.

Therefore, using the artificial neural network model 1000 trained as described above, the analysis result and/or medical information necessary for the medical diagnosis can be extracted from the medical image of a patient. For example, by using the artificial neural network model 1000, data and/or information associated with at least one of normal cells, normal epithelial, normal stroma, tumor cells (or cancer cell), cancer epithelial, cancer stroma, lymphocyte cell, necrosis, fat, and background can be extracted from the medical image.

Figure 11:
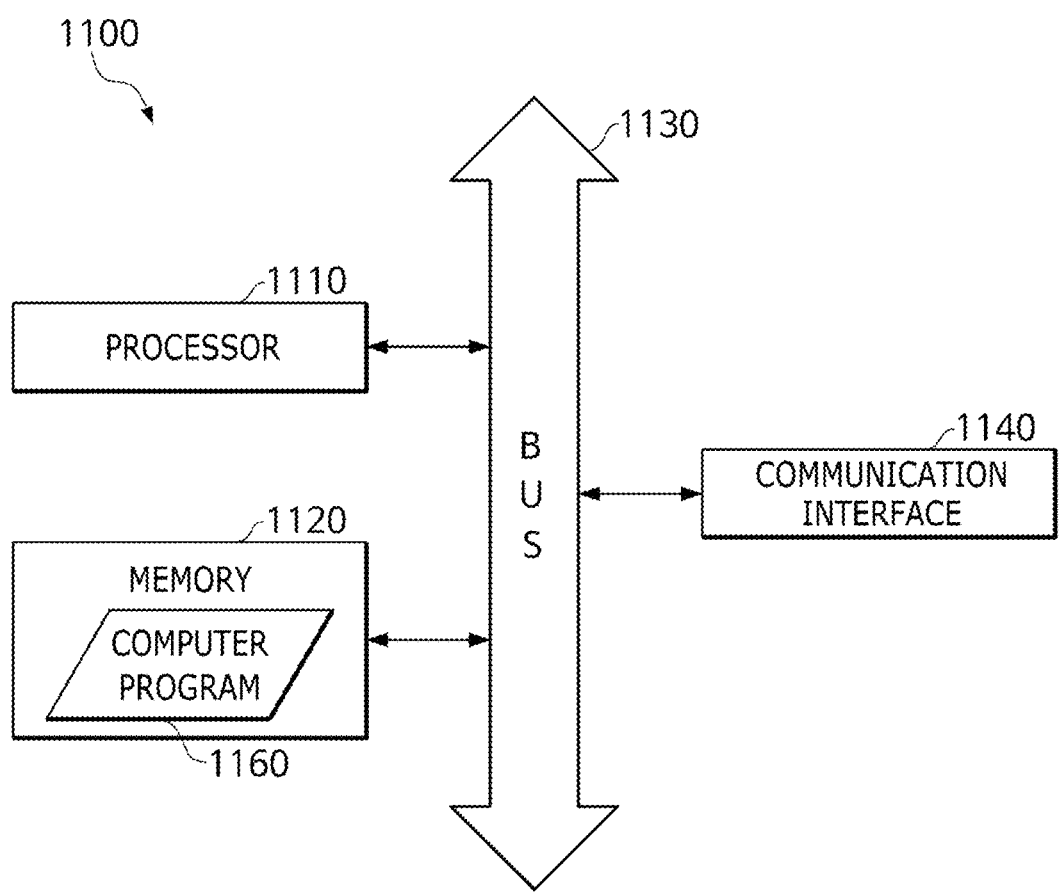
FIG. 11 is an exemplary system configuration for performing parallel processing of a medical image.

FIG. 11 is an exemplary system configuration for performing parallel processing of a medical image. An information processing system 1100 of FIG. 11 may be an example of the information processing system 200 described with reference to FIG. 2. As illustrated, the information processing system 1100 includes one or more processors 1110, a bus 1130, a communication interface 1140, and a memory 1120 for loading a computer program 1160 executed by the processor 1110. Meanwhile, only the components related to the present example are illustrated in FIG. 11. Accordingly, those of ordinary skill in the art to which the present disclosure pertains will be able to recognize that other general-purpose components may be further included in addition to the components illustrated in FIG. 11.

The processors 1110 control the overall operation of components of the information processing system (e.g., the information processing system 200). In present disclosure, the processor 1110 may be configured with a plurality of processors. The processor 1110 may include central processing unit (CPU), micro processor unit (MPU), micro controller unit (MCU), graphic processing unit (GPU), field programmable gate array (FPGA), at least two of any types of processors well known in the technical field of the present disclosure. In addition, the processors 1110 may perform an arithmetic operation on at least one application or program for executing the method according to various examples.

The memory 1120 may store various types of data, instructions, and/or information. The memory 1120 may load one or more computer programs 1160 in order to execute the method/operation according to various examples. The memory 1120 may be implemented as a volatile memory such as RAM, but the technical scope of the present disclosure is not limited thereto. For example, the memory 1120 may include a nonvolatile memory such as a read only memory (ROM), an erasable programmable ROM (EPROM), an electrically erasable programmable ROM (EEPROM), a flash memory, and the like, a hard disk, a detachable disk, or any type of computer-readable recording medium well known in the art to which the present disclosure pertains.

The bus 1130 may provide a communication function between components of the information processing system. The bus 1130 may be implemented as various types of buses such as an address bus, a data bus, a control bus, or the like.

The communication interface 1140 may support wired/wireless Internet communication of the information processing system. In addition, the communication interface 1140 may support various other communication methods in addition to the Internet communication. To this end, the communication interface 1140 may include a communication module well known in the technical field of the present disclosure.

The computer program 1160 may include one or more instructions that cause the processors 1110 to perform operations/methods in accordance with various examples. That is, the processors 1110 may perform operations/methods according to various examples by executing one or more instructions.

For example, the computer program 1160 may include one or more instructions for extracting patches from a medical image, generating a batch using a plurality of extracted patches, outputting or extracting an analysis result from the generated batch, generating/inferring medical information based on one or more extracted analysis results, and training a machine learning model to infer an analysis result and/or medical information from the medical image using the generated batch as training data, and the like. In this case, a system for processing medical images in parallel according to some examples may be implemented through the information processing system 1100.

The above description of the present disclosure is provided to enable those skilled in the art to make or use the present disclosure. Various modifications of the present disclosure will be readily apparent to those skilled in the art, and the general principles defined herein may be applied to various modifications without departing from the spirit or scope of the present disclosure. Thus, the present disclosure is not intended to be limited to the examples described herein but is intended to be accorded the broadest scope consistent with the principles and novel features disclosed herein.

Although example implementations may refer to utilizing aspects of the presently disclosed subject matter in the context of one or more standalone computer systems, the subject matter is not so limited, and they may be implemented in conjunction with any computing environment, such as a network or distributed computing environment. Furthermore, aspects of the presently disclosed subject matter may be implemented in or across a plurality of processing chips or devices, and storage may be similarly influenced across a plurality of devices. Such devices may include PCs, network servers, and handheld devices.

Although the present disclosure has been described in connection with examples herein, it should be understood that various modifications and changes can be made without departing from the scope of the present disclosure, which can be understood by those skilled in the art to which the present disclosure pertains. In addition, such modifications and changes should be considered within the scope of the claims appended herein.

What is claimed is:

1. A method for parallel processing a digitally scanned pathology image, the method being performed by a plurality of processors and comprising:

performing, by a first processor, a first operation of generating a first batch from a first set of patches extracted from a digitally scanned pathology image and providing the generated first batch to a second processor;

performing, by the first processor, a second operation of generating a second batch from a second set of patches extracted from the digitally scanned pathology image and providing the generated second batch to the second processor; and performing, by the second processor, a third operation of outputting a first analysis result from the first batch by using a machine learning model, wherein at least a part of a time frame for the second operation performed by the first processor overlaps with at least a part of a time frame for the third operation performed by the second processor.

2. The method according to claim 1, further comprising performing, by the second processor, a fourth operation of outputting a second analysis result from the second batch by using the machine learning model, wherein
medical information associated with the digitally scanned pathology image is generated based on the first analysis result and the second analysis result.

3. The method according to claim 2, wherein:
each of the first set of patches associated with the first batch and the second set of patches associated with the second batch includes spatial information in the digitally scanned pathology image;
a processed image is generated based on the spatial information associated with each of the first set of patches and the second set of patches; and
the medical information associated with the digitally scanned pathology image is generated based on the first analysis result, the second analysis result, and the processed pathology image.

4. The method according to claim 2, wherein the generated medical information includes statistical information of the digitally scanned pathology image.

5. The method according to claim 1, wherein the digitally scanned pathology image includes a plurality of digitally scanned reference pathology images, and
the machine learning model is trained by using a plurality of batches and a plurality of reference analysis results in the plurality of digitally scanned reference pathology images.

6. The method according to claim 1, wherein the digitally scanned pathology image includes segmentation information for a specific object in the digitally scanned pathology image, and
the performing the first operation includes extracting the first set of patches that include the specific object, and generating the first batch including the extracted first set of patches.

7. The method according to claim 1, wherein the first set of patches and the second set of patches are spatially associated with each other in the digitally scanned pathology image.

8. The method according to claim 7, wherein each of one or more patches included in the first set of patches and each of one or more patches included in the second set of patches are adjacent to each other or overlapped with each other at least in part in the digitally scanned pathology image.

9. The method according to claim 1, wherein:
the performing the first operation includes performing, by the first processor, image processing on the generated first batch;
the performing the second operation includes performing, by the first processor, image processing on the generated second batch; and
the image processing on the first batch and the image processing on the second batch include at least one of contrast adjustment, brightness adjustment, saturation adjustment, blur adjustment, noise injection, random crop, or sharpening.

10. A method for parallel processing a digitally scanned pathology image, the method being performed by a plurality of processors and comprising:
performing, by a first processor, a first operation of generating a first batch from one or more first patches of a plurality of patches stored in a storage medium and providing the generated first batch to a second processor;
performing, by the first processor, a second operation of generating a second batch from one or more second patches of the plurality of patches stored in the storage medium and providing the generated second batch to the second processor; and
performing, by the second processor, a third operation of outputting a first analysis result from the first batch by using a machine learning model, wherein
at least a part of a time frame for the second operation performed by the first processor overlaps with at least a part of a time frame for the third operation performed by the second processor.

11. A non-transitory computer-readable recording medium storing instructions that, when executed by one or more processors, cause performance of the method according to claim 1.

12. An information processing system, comprising:
a memory; and
a first processor and a second processor connected to the memory and configured to execute at least one computer-readable program included in the memory, wherein
the at least one computer-readable program includes instructions for:
performing, by the first processor, a first operation of generating a first batch from a first set of patches extracted from a digitally scanned pathology image and providing the generated first batch to the second processor;
performing, by the first processor, a second operation of generating a second batch from a second set of patches extracted from the digitally scanned pathology image and providing the generated second batch to the second processor; and
performing, by the second processor, a third operation of outputting a first analysis result from the first batch by using a machine learning model, wherein
at least a part of a time frame for the second operation performed by the first processor overlaps with at least a part of a time frame for the third operation performed by the second processor.

13. The information processing system according to claim 12, wherein the at least one computer-readable program further includes instructions for performing, by the second processor, a fourth operation of outputting a second analysis result from the second batch by using the machine learning model, wherein
medical information associated with the digitally scanned pathology image is generated based on the first analysis result and the second analysis result.

14. The information processing system according to claim 13, wherein:
each of the first set of patches associated with the first batch and the second set of patches associated with the second batch includes spatial information in the digitally scanned pathology image;
a processed image is generated based on the spatial information associated with each of the first set of patches and the second set of patches; and
the medical information associated with the digitally scanned pathology image is generated based on the first analysis result, the second analysis result, and the processed pathology image.

15. The information processing system according to claim 13, wherein the generated medical information includes statistical information of the digitally scanned pathology image.

16. The information processing system according to claim 12, wherein the digitally scanned pathology image includes a plurality of digitally scanned reference pathology images, and
the machine learning model is trained by using a plurality of batches and a plurality of reference analysis results in the plurality of digitally scanned reference pathology images.

17. The information processing system according to claim 12, wherein the digitally scanned pathology image includes segmentation information for a specific object in the digitally scanned pathology image, and
the performing the first operation includes extracting a first set of patches that include the specific object, and generating a first batch including the extracted first set of patches.

18. The information processing system according to claim 12, wherein the first set of patches and the second set of patches are spatially associated with each other in the digitally scanned pathology image.

19. The information processing system according to claim 18, wherein each of one or more patches included in the first set of patches and each of one or more patches included in the second set of patches are adjacent to each other or overlapped with each other at least in part in the digitally scanned pathology image.

20. The information processing system according to claim 12, wherein:
the performing the first operation includes performing, by the first processor, image processing on the generated first batch;
the performing the second operation includes performing, by the first processor, image processing on the generated second batch; and
the image processing on the first batch and the image processing on the second batch include at least one of contrast adjustment, brightness adjustment, saturation adjustment, blur adjustment, noise injection, random crop, or sharpening.

* * * * *